United States Patent
Hoste

(10) Patent No.: US 6,508,806 B1
(45) Date of Patent: Jan. 21, 2003

(54) CATHETER WITH MULTI-LAYER WIRE REINFORCED WALL CONSTRUCTION

(75) Inventor: John H. Hoste, Fallbrook, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 64 days.

(21) Appl. No.: 09/736,912

(22) Filed: Dec. 13, 2000

(51) Int. Cl.$^7$ .............................................. A61M 25/09
(52) U.S. Cl. ........................ 604/524; 604/528; 138/124
(58) Field of Search ................................. 604/523, 524, 604/525, 526, 527, 264, 96.1, 529, 528, 96.01; 138/124

(56) References Cited

U.S. PATENT DOCUMENTS

| | | | | |
|---|---|---|---|---|
| 1,984,475 A | * | 12/1934 | Goodall | 137/90 |
| 3,924,632 A | * | 12/1975 | Cook | 128/348 |
| 4,817,613 A | | 4/1989 | Jaraczewski et al. | 128/658 |
| 4,981,478 A | * | 1/1991 | Evard et al. | 604/282 |
| 5,037,404 A | * | 8/1991 | Gold et al. | 604/282 |
| 5,176,660 A | * | 1/1993 | Truckai | 604/282 |
| 5,496,292 A | * | 3/1996 | Burnham | 604/282 |
| 5,554,139 A | * | 9/1996 | Okajima | 604/282 |
| 5,951,539 A | * | 9/1999 | Nita et al. | 604/526 |
| 6,053,903 A | * | 4/2000 | Samson | 604/526 |
| 6,143,013 A | * | 11/2000 | Samson et al. | 606/192 |
| 6,245,053 B1 | * | 6/2001 | Benjamin | 604/523 |
| 6,368,316 B1 | * | 4/2002 | Jansen et al. | 604/526 |

* cited by examiner

Primary Examiner—Charles G. Freay
Assistant Examiner—Han Lieh Liu
(74) Attorney, Agent, or Firm—Fulwider, Patton, Lee & Utecht, LLP

(57) ABSTRACT

Guiding or angiography catheters, having a catheter shaft formed of a multi-layer wire reinforced wall construction consisting of one layer of wire wrapped in a substantially circumferential manner and another layer of wire laid at an angle of about ±20° to about ±75° with respect to the longitudinal axis of the tubular shaft.

23 Claims, 2 Drawing Sheets

CATHETER WITH MULTI-LAYER WIRE REINFORCED WALL CONSTRUCTION

BACKGROUND OF THE INVENTION

The invention relates to the field of intraluminal catheters, and particularly to guiding or angiography catheters suitable for intravascular procedures such as angioplasty and/or stent deployment, and the like.

In percutaneous transluminal coronary angioplasty (PTCA) procedures, a guiding catheter having a shaped distal section is percutaneously introduced into the patient's vasculature by a conventional "Seldinger" technique and then advanced through the patient's vasculature until the shaped distal section of the guiding catheter is adjacent to the ostium of a desired coronary artery. The proximal end of the guiding catheter, which extends out of the patient, is torqued to rotate the shaped distal section. As the distal section rotates, it is guided into desired coronary ostium. The distal section of the guiding catheter is shaped so as to engage a surface of the ascending aorta and thereby seat the distal end of the guiding catheter in the desired coronary ostium and to hold the catheter in that position during the procedures when other intravascular devices such as guidewires and balloon catheters are being advanced through the inner lumen of the guiding catheter.

In the typical PTCA or stent delivery procedures, the balloon catheter with a guidewire disposed within an inner lumen of the balloon catheter is advanced within the inner lumen of the guiding catheter which has been appropriately positioned with its distal tip seated within the desired coronary ostium. The guidewire is first advanced out of the distal end of the guiding catheter into the patient's coronary artery until the distal end of the guidewire crosses a lesion to be dilated or a location where a stent is to be deployed. A balloon catheter is advanced into the patient's coronary anatomy over the previously introduced guidewire until the balloon on the distal portion of the balloon catheter is properly positioned across the lesion. Once properly positioned, the balloon is inflated with inflation fluid one or more times to a predetermined size so that in the case of the PTCA procedure, the stenosis is compressed against the arterial wall and the wall expanded to open up the vascular passageway. In the case of stent deployment, the balloon is inflated to plastically expand the stent within the stenotic region. Generally, the inflated diameter of the balloon is approximately the same diameter as the native diameter of the body lumen being dilated so as to complete the dilatation or stent deployment but not overexpand the artery wall. After the balloon is finally deflated, blood flow resumes through the dilated artery and the dilatation catheter and the guidewire can be removed therefrom.

Generally, the stent deployment occurs after a PTCA procedure has been performed at the stenotic site. However, recently, in some situations the stent deployment and lesion dilatation is accomplished simultaneously. In addition to their use in PTCA and stent delivery procedures, guiding catheters are used to advance a variety of electrophysiology catheters and other therapeutic and diagnostic devices into the coronary arteries, the coronary sinus, the heart chambers, neurological and other intracorporeal locations for sensing, pacing, ablation and other procedures. For example, one particularly attractive procedure for treating patients with congestive heart failure (CHF) involves introduction of a pacing lead into the patient's coronary sinus and advancing the lead until the distal end thereof is disposed within the patient's great coronary vein which extends from the end of the coronary sinus. A second pacing lead is disposed within the patient's right ventricle and both the left and right ventricle are paced, resulting in greater pumping efficiencies and blood flow out of the heart which minimizes the effects of CHF. Current construction of many commercially available guiding catheters include an elongated shaft of a polymeric tubular member with reinforcing strands (usually metallic or high strength polymers) within the wall of the tubular member. The strands are usually braided into a reinforcing structure. The strands are for the most part unrestrained except by the polymeric wall. The desired shape in the distal section of the catheter, which facilitates its deployment at the desired intracorporeal location, is typically formed by shaping the distal section into the desired shape and heat setting the polymeric material of the catheter wall to maintain the desired shape. There is usually some spring-back after the heat formation due to the reinforcing braid, but this is usually compensated for in the shape the catheter is held in during the heat setting.

Clinical requirements from utilization of guiding catheters to advance electrophysiology catheters and the like have resulted in an increase in the transverse dimensions of the inner lumens of guiding catheters to accommodate a greater variety of intracorporeal devices and a decrease in the outer transverse dimensions of the guiding catheter to present a lower profile and thereby facilitate advancement within the patient's body lumens and openings.

What has been needed is a catheter design which would allow for continued thinning of the catheter wall while facilitating the formation of the shape of the distal end of the catheter.

SUMMARY OF THE INVENTION

The present invention is directed to an improved catheter shaft construction which can be employed in guiding or angiography catheters for angioplasty procedures.

The catheter shaft of the invention generally includes an elongated tubular member having an inner lumen extending therein. The catheter shaft has a wall construction, which comprises a combination of multiple, preferably two layers of wire, cord or fiber reinforcement. One of them consists of a left hand and right hand set of wires wound at a lay angle of about ±20° to about ±75°, preferably about ±40° to about ±70°, most preferably about ±65°, with respect to the longitudinal axis of the tubular shaft, and the other layer of wire is wound in a substantially circumferential manner (coiled) at a preferred pitch of approximately twice the wire width along the same longitudinal axis. The circumferential coil has such a pitch as to yield a percent coverage of between about 10% and about 80%, preferably about 50%. The combination of the two layers, along with the properties of the polymer matrix used, provides the catheter shaft the desired structural properties, such as, torsional stiffness, torsional collapse load, bending stiffness, and bend kink. The structural properties of this wall construction can also be easily modified by varying one or more of the design parameters, such as wire material, wire size, wire volume fraction, braid lay angle, coil pitch or matrix polymer.

The expression "oblique wound layer" is used in the text of this application for one of the two layers of the wall construction and it represents the layer of wire braided at a lay angle of from about ±20° to about ±75°, preferably about ±40° to about ±70°, most preferably about ±65°, with respect to the longitudinal axis of the tubular shaft.

The expression "circumferential wound layer" in general refers to a coil of pitch about twice the wire width, yielding a coil coverage of about 50%. The coil coverage is defined as the ratio of wire width to pitch expressed as a percentage. This pitch may be varied to provide from about 10% coverage to about 80% coverage to accommodate the structural needs.

The wires suitable for the present invention include any stiff filamentary fibers, such as, but not limited to, carbon or boron fiber, glass, ceramic or graphite non-metallic wires, Kevlar (polyaramid), metallic wires such as stainless steel ribbons or a superelastic metal such as Nitinol, natural and synthetic fibers such as nylon, and polyesters fibers. The wire reinforcement of the oblique wound layer can be braided or filament wound. If braided, a triaxial braid may be used incorporating longitudinal fibers of the same or different fiber material.

The two layers of wire reinforcement are surrounded and stabilized by a polymer matrix which is formed of any polymer or elastomeric compound such as, but not limited to, nylons, polyurethanes, polyesters, polyimides, rubbers, silicone, PEEK or polytetrafluoroethylene (PTFE or Teflon). The polymeric material may be applied to the wires before or after they are braided/wounded to a tubular structure. The impregnation of the stabilizing matrix can be carried out by a variety of known processes, such as extrusion, pultrusion, molding or shrink tubing.

The two wire layers can be formed in either order; the substantially circumferential wound layer innermost or the oblique wound layer innermost. If the substantially circumferential wound layer composed of preferably round wire is the innermost wire layer and the oblique wound layer is the outer layer to the innermost wire layer, a closely wound inner wire would form a relatively smooth inner surface of the catheter shaft without the need of an additional inner polymeric liner. However, a lubricious coating may be added to the inner wire surface if required.

Alternatively, the oblique wound layer can be the innermost wire layer, and the substantially circumferential wound layer is the outer layer to the innermost wire layer. In this construction, the stabilizing polymer matrix surrounding the innermost oblique wound layer may also form a smooth inner surface. A lubricious coating may be optionally added to the inner surface.

As a presently preferred embodiment of the invention, a guiding catheter comprises an elongated shaft having an inner lumen extending therein. The catheter has the dual layer wire reinforced wall construction as described above. The distal portion of the catheter is given a shape (e.g., Judkins or Amplatz shapes) to facilitate the advancement and seating thereof within a desired coronary ostium and the distal tip is provided with a soft tip construction, such as described in U.S. Pat. No. 5,234,416 which is incorporated herein by reference.

The present invention not only offers reduction in wall thickness, thereby allowing larger lumens, but also provides the guiding catheter a significant increase in torque transmission and collapse performance. Furthermore, the dual layer wall construction of the present invention allows a greater degree of design freedom to meet the structural objectives. These and other advantages of the invention will become more apparent from the following detailed description of the invention when taken in conjunction with the accompanying drawings.

DETAILED DESCRIPTION OF THE INVENTION

Figure 1:
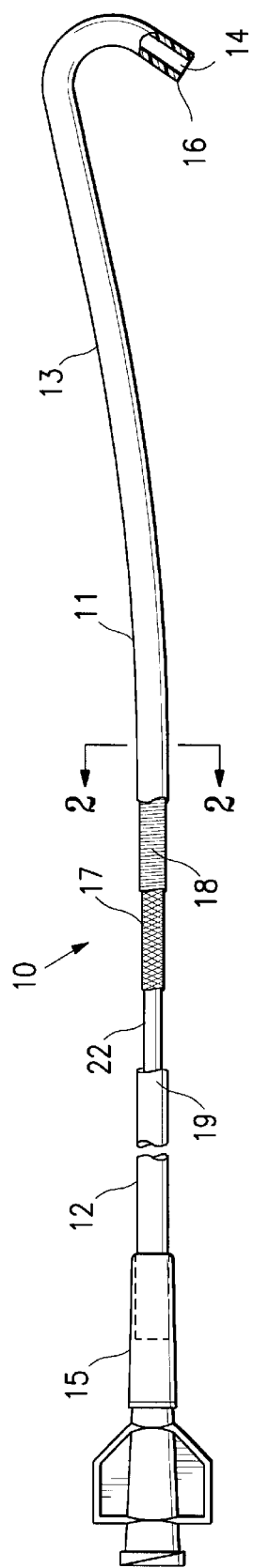
FIG. 1 is a schematic, elevational view of a guiding catheter embodying features of the invention.
Figure 2:
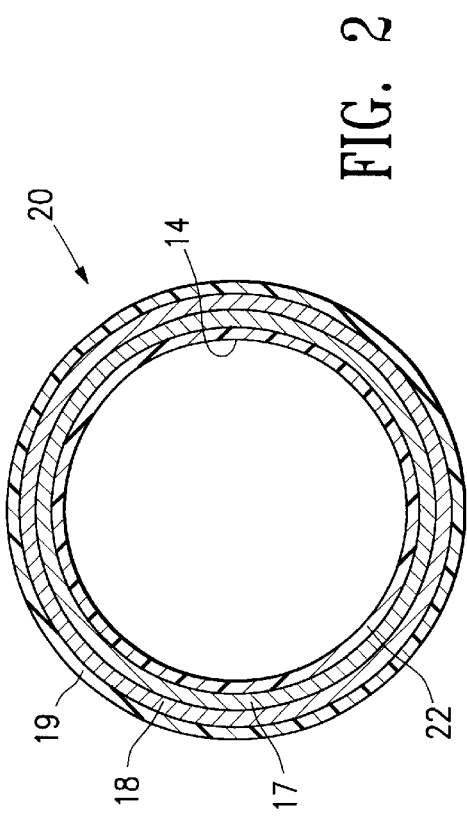
FIG. 2 is a transverse cross-sectional view of the guiding catheter shown in FIG. 1 taken along the lines 2—2.

FIGS. 1 and 2 schematically illustrate a guiding catheter 10 of the invention which generally includes an elongated catheter shaft 11 having a proximal section 12, a more flexible distal section 13, an inner lumen 14 extending therein, a Luer hub 15 on the proximal end of the shaft and a nontraumatic distal tip 16. The distal section 13 of the shaft 11 is shaped to facilitate the entry thereof into the ostium of a desired coronary artery. As will be appreciated by those skilled in the art, the J-shape of the distal section 13 of the catheter shown in FIG. 1 is a schematic representation and a variety of shapes, such as the well-known Judkins and Amplatz configurations for both the right and left coronary arteries, may also be employed to facilitate the entry of the distal tip of the guiding catheter into the ostium of the desired coronary artery. The relatively soft nontraumatic distal tip 16 is intended to minimize traumatic engagement with arterial tissue.

The wall of the catheter shaft 11 is formed of an oblique wound layer 17 of from about ±20° to about ±75°, preferably about ±40° to about ±70°, most preferably about ±65°, and a second layer of the substantially circumferential wound layer 18. The order of the two layers may be reversed.

FIG. 2 illustrates the wall construction of the shaft 11 of catheter 10. The dual layer wire reinforced wall construction 20 consisting of an oblique wound layer 17 of from about ±90° to about ±75°, preferably about ±40° to about ±70°, most preferably about ±65°, and a second layer of the substantially circumferential wound layer 18 having such as pitch as to yield a percent coverage of between about 10% and about 80%, preferably about 50%, defines the inner lumen 14. The wall construction 20 has a coating or outer jacket 19 and preferably a liner 22 interior to the innermost wire layer. The dual layer wire reinforced wall construction 20 is radially compressed against a removable mandrel (not shown)

Figure 3:
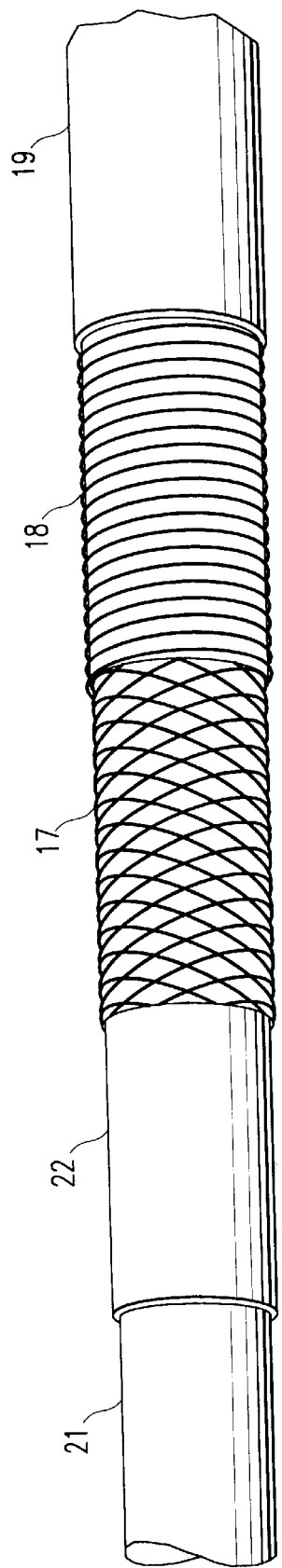
FIG. 3 is an enlarged view of the wall construction in the fabrication process, showing the dual layers, the liner and jacket/coating.

FIG. 3 depicts an enlarged view of the dual layer wire reinforced wall construction. The inner layer 17 is the oblique wound layer and the outer layer 18 is the substantially circumferential wound layer. The exterior of the dual layer wire reinforced wall construction is provided with an outer coating or jacket 19 and the interior a liner 22, formed of a polymer matrix. The mandrel 21 is removed after fabrication. While the oblique wound layer is shown in this figure as the inner layer and the substantially circumferential wound layer as the outer layer, the two layers may be reversed to accommodate the desired mechanical properties of the shaft section.

The wires employed to form the wire reinforcement layers is preferably about 0.5 to about 3.5 mil in diameter and may be formed from any stiff filamentary fibers, such as, carbon or boron fiber, glass, ceramic or graphite non-metallic wires, Kevlar (polyaramid), metallic wires such as stainless steel ribbons, natural and synthetic fibers such as nylon and polyester fibers. For a 5F or 6F catheter, the substantially circumferential wound layer is preferably formed from a 304V stainless steel 0.001 inch diameter wire and the oblique wound layer is preferably formed from a 304V stainless steel 1×5 mil flat wire. The wire dimensions are dependent on the French size of the given catheter.

As a presently preferred embodiment of the invention, the substantially circumferential wound layer of 304V round wire at about 50% of wire coverage is the inner layer and an oblique wound layer of 304V flat wire at a lay angle of about ±65° is the outer layer. The wire layers are fully impregnated with a flexible polymer matrix, and covered by an exterior coating/jacket. In this currently preferred embodiment, there is a thin polymer liner as the innermost layer and a lubricious coating may be applied to the innermost lumen surface and/or the exterior surface.

Figure 4:
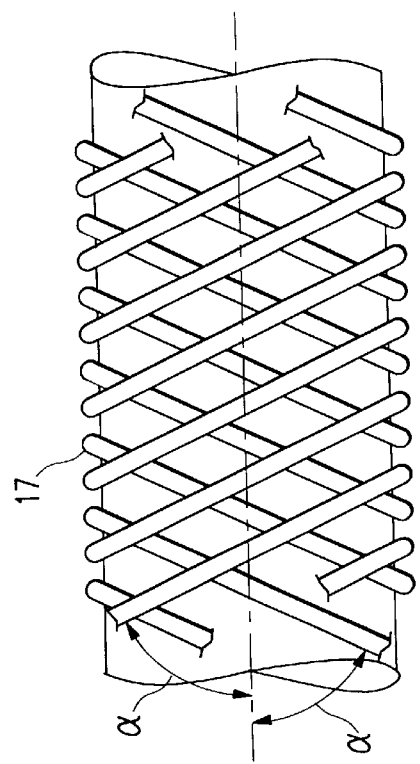
FIG. 4 is a schematic view of wire being wrapped onto a tubular structure at an angle of ±65°.

In a typical form of a guiding catheter as shown in FIG. 1, the wire for the oblique wound layer, in general, has a thickness of from about 0.0005 inch (0.0127 mm) to about 0.0025 inch (0.0635 mm), preferably about 0.001 inch (0.0254 mm) and a width of from about 0.002 inch (0.0508 mm) to about 0.015. inch (0.381 mm), preferably about 0.005 inch (0.127 mm). For this layer, the wire is braided from the proximal end of a mandrel to the desired distal terminal point at a desired angle between about 20° and about 75°, preferably about 65°, with respect to the longitudinal axis of the tubular shaft as shown in FIG. 4. Alternatively, the oblique wound layer could be filament wound from the proximal end of a mandrel to the distal terminal point at a desired angle between about 20° and about 75°, preferably about 65°, with respect to the longitudinal axis of the tubular shaft as shown in FIG. 4. The direction of winding is reversed at the distal terminal point, with the angle remaining the same but in a direction 130° from the first direction (i.e., about −65° with respect to the longitudinal axis of the tubular shaft) and the wrapping is continued to the proximal end of the mandrel. A plurality of wires, preferably 1 to 4, may be wrapped in parallel onto the mandrel. If the oblique wound layer is the second layer, the wrapping is applied to the previously applied circumferential wound layer instead of the mandrel.

Figure 5:
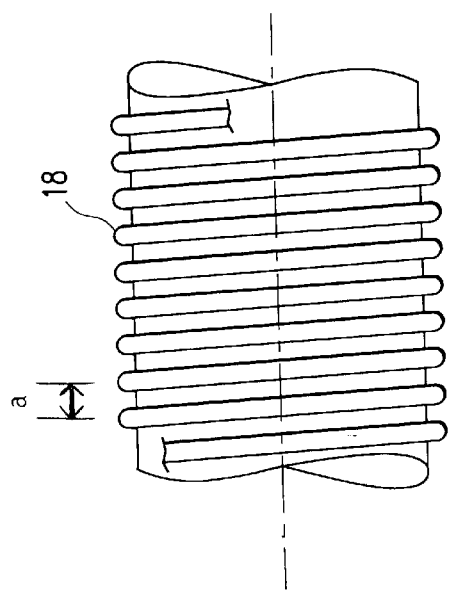
FIG. 5 is a schematic view of wire being substantially circumferentially wound onto a tubular structure.

The wire used for the substantially circumferential wound layer has a diameter of about 0.0005 inch to about 0.0025 inch, preferably a diameter of 0.001 inch. Alternatively, the substantially circumferential wound layer could use flat wire having a thickness of about 0.0005 inch to about 0.0025 inch, preferably about 0.001 inch, and a width of about 0.001 inch to about 0.010 inch, preferably about 0.005 inch. If it is the inner layer, the wire is wrapped about a mandrel, with or without intermediate layers or structures, at a nominal pitch "a" yielding about 50% coverage of the tubular shaft as shown in FIG. 5. If it is the outer layer, the wire is wrapped in the same manner about the previously applied oblique wound layer.

After the wrapping operation is completed, a polymer material is applied to the layers for forming a stabilizing matrix. At the same time the impregnating polymer could be made to form an interior liner for the lumen and/or an exterior jacket. Suitable polymeric materials, thermoplastic or thermoset, include nylons, polyurethanes, polyesters, polyimides, rubbers, silicone, PEEK, polytetrafluoroethylene (PTFE or Teflon) and the like. The polymeric material may, in addition to or alternatively, be applied to the wires before braiding/wrapping. Impregnation of the wire layers with the polymer is required to stabilize the wire structure to form a flexible matrix composite material. Those skilled in the art will recognize a number of different means for accomplishing the impregnation, depending on whether the polymer is a thermoplastic or thermoset material. For example, if the polymer material is thermoplastic, a shrink jacket process, an extrusion process or a matched mold process may be used. If the polymer material is thermoset, a molding process, a liquid dipping process or an extrusion-like process may be used. All of these processes and modifications thereof are well-known to those skilled in the art. Final outer diameters can be achieved by a grinding process if desired.

The mandrel is removed after the stabilizing polymer matrix or the heat shrunk outer jacket is formed. If necessary, a lubricious coating may be applied to the inner or exterior surfaces of the wall construction. Alternatively, a thin inner tubular member formed of suitable lubricous material such as fluorinated ethylene propylene or polytetrafluoroethylene (e.g. Teflons® sold by E.l. duPont, deNemours & Co.) may be employed over the mandrel and become a member of the shaft wall construction upon removal of the innermost tubular construction mandrel. In either case, the tubular structure has an inner lumen with very low frictional characteristics which is highly desirable in guiding catheters to facilitate the advancement of guidewires and dilatation catheters therethrough.

The outer diameter of the shaft with dual layer wire reinforced wall construction may range from about 0.040 inch to about 0.200 inch (1.016–5.080 mm). The overall length of the catheter for coronary angioplasty typically range from about 80 to about 125 cm.

While the invention has been describe herein primarily directed to guiding and angiography catheters, those skilled in the art will recognize that the catheter shaft of the present invention may be utilized for other types of catheters used in a wide variety of body lumens, e.g. balloon catheters for prostatic urethral dilatation. Moreover, to the extent not specifically described herein, conventional materials and methods of manufacturing can be employed to form the catheters of the invention. Various modifications and improvements may be made to the invention without departing from the scope thereof.

What is claimed is:

1. A dual layer wire reinforced wall construction of a guiding catheter comprising a tubular shaft having one layer of wire wrapped in a substantially circumferential manner wherein the circumferentially wrapped layer provides torsional collapse strength; and an oblique wound layer of wire wound at an angle from the longitudinal axis of the tubular shaft wherein the oblique wound layer provides torsional stiffness.

2. The dual layer wire reinforced wall construction of claim 1 wherein said 20° to 75° or about −20° to about −75°.

3. The dual layer wire reinforced wall construction of claim 1 wherein the substantially circumferential wound layer is the inner layer.

4. The dual layer wire reinforced wall construction of claim 1 wherein the oblique wound layer is the inner layer.

5. The dual layer wire reinforced wall construction of claim 1 wherein said oblique wound layer is filament wound.

6. The dual layer wire reinforced wall construction of claim 1 wherein said circumferential wound layer may vary in its pitch to yield from about 10% to about 80% wire coverage.

7. The dual layer wire reinforced wall construction of claim 2 wherein said oblique wound layer is at about ±650 from the longitudinal axis of the tubular shaft.

8. The dual layer wire reinforced wall construction of claim 1 wherein the wires are selected from a group consisting of carbon fiber, boron fiber, glass, ceramic non-metallic wires, graphite non-metallic wires, polyaramid, metallic wires, natural fibers and synthetic fibers.

9. The dual layer wire reinforced wall construction of claim 8 wherein the metallic wires are selected from a group consisting of stainless steel ribbons and superelastic metal; and wherein the synthetic fibers are selected from a group consisting of nylon fibers and polyester fibers.

10. The dual layer wire reinforced wall construction of claim 1 which is stabilized in a polymeric matrix.

11. The dual layer wire reinforced wall construction of claim 10 wherein the polymer is selected from a group consisting of nylons, polyurethanes, polyesters, polyimides, rubber, silicone, polyesters, PEEK and polytetrafluoroethylenes or other thermopastic or thermoset polymers.

12. A guiding or angiography catheter for performing diagnostic or therapeutic procedures within a patient's arterial system comprising a tubular shaft of dual layer wire reinforced wall construction comprising one layer of wire wrapped in a substantially circumferential manner wherein the circumferentially wrapped layer provides torsional collapse strength; and an oblique wound layer of wire wound at an angle from the longitudinal axis of the tubular shaft wherein the oblique wound layer of wire provides torsional stiffness.

13. The guiding or angiography catheter of claim 12 wherein said about 20° to 75° or about −20° to about −75°.

14. The guiding or angiography catheter of claim 13 wherein said oblique wound layer is wound at about ±65° from the longitudinal axis of the tubular shaft.

15. The guiding or angiography catheter of claim 12 wherein the catheter has a J-shaped distal end to facilitate advancement and entry into a patient's coronary ostium.

16. The guiding or angiography catheter of claim 12 including a soft distal tip to prevent or minimize traumatic engagement with blood vessel lining.

17. A method of forming a shaft with a dual layer wire reinforced wall construction, comprising the following steps not in any particular order:

a) wrapping over a tubular structure a wire in a substantially circumferential manner wherein the circumferentially wrapped layer provides torsional collapse strength; and b) winding wire onto the tubular structure at an angle from the longitudinal axis of the tubular shaft wherein the wire wound at the angle from the longitudinal axis provides torsional stiffness.

18. The method of claim 17 wherein said oblique wound layer is wound at an 20° to 75° or about −20° to about −75° from the longitudinal axis of the tubular shaft.

19. The method of claim 18 wherein the angle is about ±65°.

20. The method of claim 17 wherein the circumferential wound layer has a pitch as to yield a percent wire coverage of about 10% to about 80%.

21. The method of claim 17 further comprising a step of forming a stabilizing matrix impregnating the layers.

22. The method of claim 17 further comprising a step of forming a polymer coat/jacket over the tubular structure.

23. The method of claim 17 further comprising a step of forming a polymer inner liner within the tubular structure.

* * * * *

UNITED STATES PATENT AND TRADEMARK OFFICE
CERTIFICATE OF CORRECTION

PATENT NO. : 6,508,806 B1
DATED : January 21, 2003
INVENTOR(S) : John H. Hoste

It is certified that error appears in the above-identified patent and that said Letters Patent is hereby corrected as shown below:

Column 6,
Line 50, after "said", add -- angle is about --.

Column 7,
Line 26, after "said", add -- angle is --.

Column 8,
Line 17, after "an", add -- angle of about --.

Signed and Sealed this

Twenty-fifth Day of March, 2003

JAMES E. ROGAN
*Director of the United States Patent and Trademark Office*